United States Patent
Learmonth et al.

(10) Patent No.: US 8,546,571 B2
(45) Date of Patent: Oct. 1, 2013

(54) CATALYTIC HYDROGENATION OF ENE-CARBAMATES

(75) Inventors: David Alexander Learmonth, Alfena (PT); Antonio Zanotti-Gerosa, Cambridge (GB); Gabriela Alexandra Grasa, Mantua, NJ (US); Alexander Beliaev, Vila do Conde (PT)

(73) Assignee: BIAL—Portela & C.A., S.A., S. Mamede Do Coronado (PT)

( * ) Notice: Subject to any disclaimer, the term of this patent is extended or adjusted under 35 U.S.C. 154(b) by 113 days.

(21) Appl. No.: 12/518,416

(22) PCT Filed: Dec. 12, 2007

(86) PCT No.: PCT/GB2007/004756
§ 371 (c)(1),
(2), (4) Date: Aug. 5, 2009

(87) PCT Pub. No.: WO2008/071951
PCT Pub. Date: Jun. 19, 2008

(65) Prior Publication Data
US 2010/0036127 A1  Feb. 11, 2010

Related U.S. Application Data

(60) Provisional application No. 60/869,605, filed on Dec. 12, 2006.

(51) Int. Cl.
- *C07F 9/00* (2006.01)
- *C07F 9/50* (2006.01)
- *C07D 233/00* (2006.01)
- *C07D 233/04* (2006.01)
- *C07D 311/00* (2006.01)
- *C07D 311/04* (2006.01)

(52) U.S. Cl.
USPC .......................... 546/21; 548/311.4; 549/404

(58) Field of Classification Search
None
See application file for complete search history.

(56) References Cited

U.S. PATENT DOCUMENTS

| 5,420,151 | A | | 5/1995 | Hammarberg et al. | |
|---|---|---|---|---|---|
| 5,886,182 | A | * | 3/1999 | Chan et al. ...................... | 546/21 |

FOREIGN PATENT DOCUMENTS

| EP | 1408038 A2 | 4/2004 |
|---|---|---|
| WO | 9015790 A1 | 12/1990 |
| WO | 9529165 A2 | 11/1995 |
| WO | 2004033447 A1 | 4/2004 |
| WO | 2008071951 A2 | 6/2008 |
| WO | 2008071951 A3 | 6/2008 |

OTHER PUBLICATIONS

Foreign communication from a related counterpart application—Preliminary Search Report, PT 103901, Apr. 10, 2008, 1 page.
Baxter, A.D., et al., "Enantiospecific synthesis of R- and S-5,6-dihydroxy-2-(N,N-Dl-n-propylamino)tetralins from serine," Tetrahedron Letters, 1992, pp. 2331-2334, vol. 33, No. 17, Pergamon Press, XP002476037.
Cannon, Joseph G., et al., "5,7-dihydroxy-2-aminotetralin derivatives: synthesis and assessment of dopaminergic and adrenergic actions," J. Med. Chem.,1981, pp. 149-153, vol. 24, No. 2, American Chemical Society, XP002476045.
Cecchi, R., et al., "Synthesis and β-adrenergic activity of atypical β-adrenergic phenylethanolaminotetralin steroisomers," Eur. J. Med. Chem., 1994, pp. 259-267, vol. 29, No. 4, Elsevier, Paris, XP002476036.
Charlton, James L., et al., "An asymmetric synthesis of 2-amino-6,7-dihydroxy-1,2,3,4-tetrahydronaphthalene (ADTN)," Can. J. Chem., 1990, pp. 2028-2032, vol. 68, No. 11, XP002476039.
Crowley, G. P., et al., "Experiments on the synthesis of substances related to the sterols. Part XXIV. Some derivatives of β-tetralone," J. Chem. Soc., 1938, pp. 2001-2005, XP009098607.
Dupau, Philippe, et al., "Direct preparation of n-(alk-1-en-1-yl)carbamates from cyclic ketones and unsubstituted carbamates," Collect. Czech. Chem. Commun., 2002, pp. 235-244, vol. 67, No. 2, XP009098514.
Dupau, Philippe, et al., "New route to optically active amine derivatives: ruthenium-catalyzed enantioselective hydrogenation of ene carbamates,"Tetrahedron: Asymmetry, 1999, pp. 3467-3471, vol. 10, Pergamon, Elsevier Science Ltd., XP002476034.

(Continued)

*Primary Examiner* — Janet Andres
*Assistant Examiner* — Timothy R Rozof
(74) *Attorney, Agent, or Firm* — Conley Rose, P.C.; Rodney B. Carroll

(57) ABSTRACT

A process for preparing the S or R enantiomer of a compound of formula A,

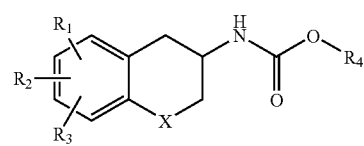

the process comprising subjecting a compound of formula B to asymmetric hydrogenation in the presence of a chiral catalyst and a source of hydrogen,

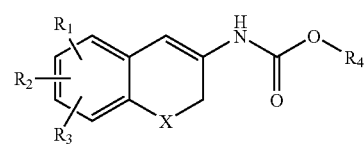

wherein: X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

52 Claims, No Drawings

(56) References Cited

OTHER PUBLICATIONS

Dupau, Philippe, et al., "Synthesis of optically active 2-aminotetraline derivatives via enantioselective ruthenium-catalyzed hydrogenation of ene carbamates," Tetrahedron: Asymmetry, 2001, pp. 863-867, vol. 12, No. 6, Pergamon, Elsevier Science Ltd., Amsterdam, XP004241708.

Goeksu, Suleyman, et al., "A concise synthesis of 2-amino-1,2,3,4-tetrahydronaphthalene-6,7-diol('6,7-ADTN') from naphthalene-2,3-diol," Helvetica Chemica Acta, 2003, pp. 3310-3313, vol. 86, No. 10, XP002476032.

Goeksu, Suleyman, et al., "An alternative synthesis of the dopaminergic drug 2-amino-1,2,3,4-tetrahydronaphthalene-5,6,diol (5,6-ADTN)," Helvetica Chemica Acta, 2006, pp. 270-273, vol. 89, No. 2, XP002476031.

Greene, Theodora W., et al., "Protective groups in organic synthesis," Second Edition, 1991, pp. 315-348, John Wiley and Sons, Inc., Wiley-Interscience Publication.

Langlois, Michel, et al., "A new synthesis of 8-hydroxy-2d1-n-propylamino-tetralin (8-oh-dpat)," Synth. Commun., 1992, pp. 1723-1734, vol. 22, No. 12, Marcel Dekker, Inc., XP009098506.

Mori, Kazuki, et al., "Synthesis of spirodienone derivatives and their conversion into dihydrobenzopyrans," Tetrahedron, 2001, pp. 5533-5542, vol. 57, No. 26, Pergamon, Elsevier Science Ltd., XP002476033.

Nichols, David E., et al., "Potential Psychotomimetics, 2, Rigid analogs of 2,5-dimethoxy-4-methylphenylisopropylamine (dom, stp)," J. Med. Chem., 1974, pp. 161-166, vol. 17, No. 2, XP002476046.

Orlek, Barry S., et al., "Stereoselective synthesis of protected amines and diamines from alkenes using n,n-dichloro-t-butylcarbamate," Tetrahedron Letters, 1991, pp. 4045-4048, vol. 32, No. 32, Pergamon Press, Great Britain, XP002476038.

Rezaie, R., et al., "5-Substituted 3,4-dihydro-3-amino-2H-1-benzopyran derivatives: synthesis and interaction with serotoninergic receptors," Journal of Pharmacy and Pharmacology, 2001, pp. 959-968, vol. 53, No. 7, XP009098520.

Soyka, Rainer, et al., "6,6-Disubstituted hex-5-enoic acid derivatives as combined thromboxane A2 receptor antagonists and synthetase inhibitors," 1994, J. Med. Chem., pp. 26-39, vol. 37, No. 1, American Chemical Society, XP002476035.

Wan, Kam-To, et al., "Ruthenium (II)-sulfonated BINAP: a novel water-soluble asymmetric hydrogenation catalyst," Tetrahedron: Asymmetry, 1993, pp. 2461-2468, vol. 4, No. 12, Pergamon Press Ltd., XP002024976.

Waser, Ernst, Uber einige derivate des ac.-tetrahydro-beta-naphthylamins, Chem Ber., 1916, pp. 1202-1207, vol. 49, XP009098498.

Weinstock, Joseph, et al., "Synthesis and dopaminergic activity of some halogenated mono- and dihydroxylated 2-aminotetralins," 1986, J. Med. Chem., pp. 1615-1627, vol. 29, No. 9, American Chemical Society, XP002476040.

Yanagi, Takashi, et al., "The practical synthesis of (2s)-7-methoxy-1,2,3,4-tetrahydro-2-naphthylamine via optical resolution of 2-(3-methoxybenzyl)succinic acid," Chem. Pharm. Bull., 2001, pp. 340-344, vol. 49, No. 3, Pharmaceutical Society of Japan, XP009098513.

Foreign communication from the priority application—International Search Report and Written Opinion, PCT/GB2007/004756, Aug. 13, 2008, 23 pages.

Foreign communication from the priority application—International Preliminary Report on Patentability, PCT/GB2007/004756, Jun. 25, 2009, 13 pages.

U.S. Appl. No. 60/869,605, filed Dec. 12, 2006 and entitled "Process".

Foreign communication from a related counterpart application—European Examination Report, EP 07848500.0, May 23, 2012, 6 pages.

* cited by examiner

CATALYTIC HYDROGENATION OF ENE-CARBAMATES

CROSS-REFERENCE TO RELATED APPLICATIONS

This application is a filing under 35 U.S.C. 371 of International Application No. PCT/GB2007/004756 filed Dec. 12, 2007, entitled "Process," claiming priority of U.S. Provisional Patent Application No. 60/869,605 filed Dec. 12, 2006, which applications are incorporated by reference herein in their entirety.

FIELD OF THE INVENTION

The present invention relates to an improved catalytic process for asymmetric hydrogenation. In particular, the present invention relates to a process for preparing novel intermediates useful in the synthesis of peripherally-selective inhibitors of dopamine-β-hydroxylase, the process involving catalytic asymmetric hydrogenation. The present invention also relates to a new transition metal complex, useful in the catalytic asymmetric hydrogenation.

BACKGROUND OF THE INVENTION (R)-5-(2-Aminoethyl)-1-(6,8-difluorochroman-3-yl)-1,3-dihydroimidazole-2-thione hydrochloride (the compound of formula P, below) is a potent, non-toxic and peripherally selective inhibitor of DβH, which can be used for treatment of certain cardiovascular disorders. Compound P is disclosed in WO2004/033447, along with processes for its preparation.

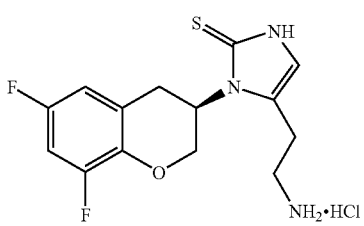

P

The process disclosed in WO2004/033447 involves the reaction of (R)-6,8-difluorochroman-3-ylamine hydrochloride (the structure of (R)-6,8-difluorochroman-3-ylamine is shown below as compound Q), [4-(tert-butyldimethylsilanyloxy)-3-oxobutyl]carbamic acid tert-butyl ester and potassium thiocyanate.

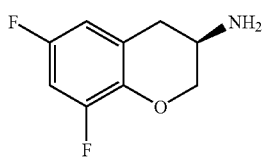

Q (R)-6,8-difluorochroman-3-ylamine (compound Q) is a key intermediate in the synthesis of compound P. The stereochemistry at the carbon atom to which the amine is attached gives rise to the stereochemistry of compound P, so it is advantageous that compound Q is present in as pure a form as possible. In other words, the R enantiomer of compound Q should be in predominance, with little or no S enantiomer present. Thus, the process for preparing compound Q will advantageously produce compound Q with as high an enantiomeric excess (e.e) as possible.

SUMMARY OF THE INVENTION

An advantageous process for preparing a precursor of, for example, the compound of formula Q has now been found. The process involves catalytic asymmetric hydrogenation of a corresponding novel ene-carbamate. The process may also be employed in the preparation of similar precursors useful in the production of other peripherally-selective inhibitors of dopamine-β-hydroxylase. A new transition metal complex, which may be employed in the catalytic asymmetric hydrogenation process has also been found. The complex is particularly advantageous as it shows high activity and selectivity in the asymmetric hydrogenation reaction. Levels of activity and selectivity have also been shown to be improved when the hydrogenation is carried out in the presence of acid additives.

The hydrogenation of ene-carbamates using Ru-BINAP and Ru-DuPhos catalysts is described in Dupau, P.; Bruneau, C.; Dixneuf, P. H. Tet. Asymm. 1999, 10, 3467-3471; and in Dupau, P.; Hay, A.-E.; Bruneau, C.; Dixneuf, P. H. Tet. Asymm. 2001, 12, 863. The maximum e.e's obtained with either system are up to 76 (92 for one particular substrate).

DETAILED DESCRIPTION

According to a first aspect of the present invention, there is provided a process for preparing the S or R enantiomer of a compound of formula A,

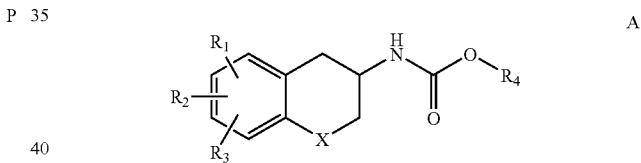

A the process comprising subjecting a compound of formula B to asymmetric hydrogenation in the presence of a chiral catalyst and a source of hydrogen,

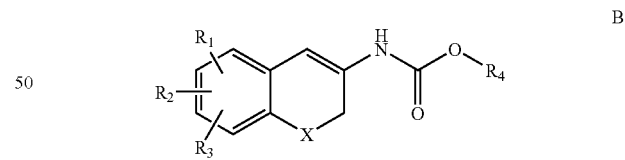

B wherein: X is CH2, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine. Compound B may be referred to as an ene-carbamate.

Throughout the specification, unless stated otherwise, the terms 'alkoxy' and 'alkyloxy' are equivalent.

In an embodiment, X is O. In another embodiment, at least one of $R_1$, $R_2$ and $R_3$ is fluorine. Suitably, compound A has the following formula:

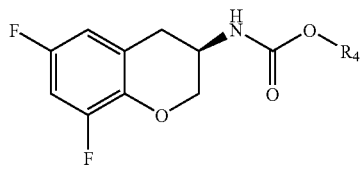

In an embodiment, $R_4$ is $C_1$ to $C_4$ alkyl. Optionally, $R_4$ is methyl (i.e. the methyl-substituted ene-carbamate), ethyl (i.e. the ethyl-substituted ene-carbamate) or t-Bu (i.e. the t-Bu-substituted ene-carbamate). Preferably, $R_4$ is methyl. In an alternative embodiment, $R_4$ is benzyl (i.e. the benzyl-substituted ene-carbamate).

The chiral catalyst may comprise a transition metal complex comprising a chiral ligand. Suitably, the catalyst has the formula [(bisphosphine)Ru(arene)X']Y, [(bisphosphine)Ru(L)$_2$] or [(bisphosphine)Ru(L')$_2$X'$_2$], wherein the bisphosphine is chiral, X' is a singly-negative monodentate ligand, Y is a balancing anion, L is a monovalent negative coordinating ligand and L' is a non-ionic monodentate ligand.

Examples of the bisphosphine ligands that can be used in the asymmetric hydrogenation of the present invention are shown in Scheme 1 below. Bisphosphine ligands having the opposite stereochemistry to that of the ligands in scheme 1 may also be used in the asymmetric hydrogenation of the present invention.

Scheme 1

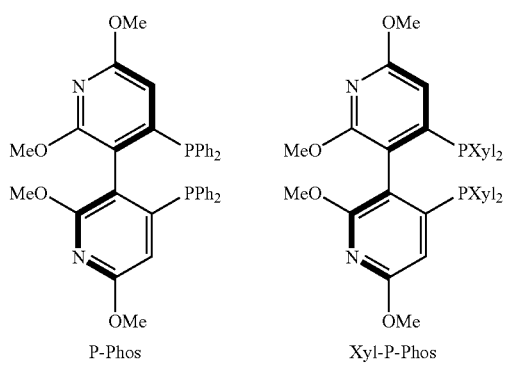

P-Phos        Xyl-P-Phos

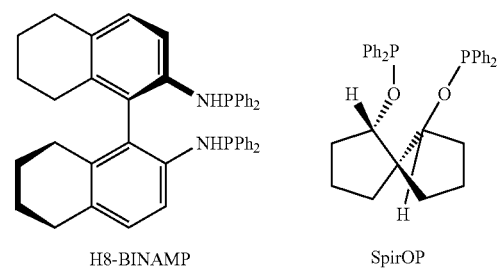

H8-BINAMP        SpirOP

-continued

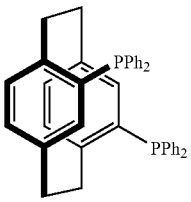 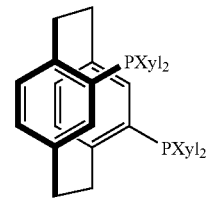

Phanephos        Xyl-Phanephos

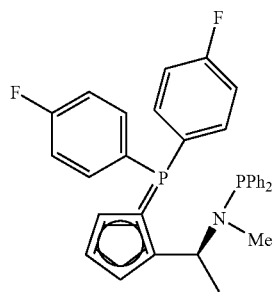

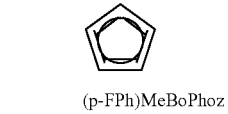

MeBoPhoz        (p-FPh)MeBoPhoz

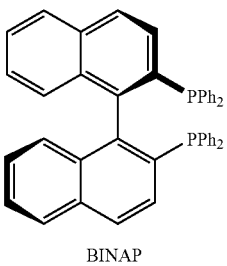 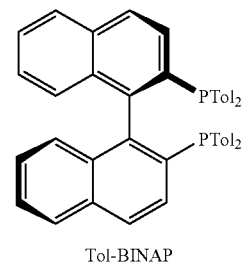

BINAP        Tol-BINAP

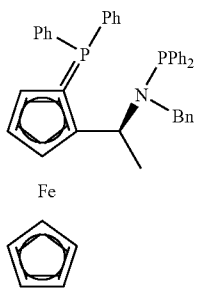

BnBoPhoz

In an embodiment, the bisphosphine may be the R or S enantiomer of BINAP or TolBINAP. Alternatively, the bisphosphine may be the R or S enantiomer of a compound having the following formula

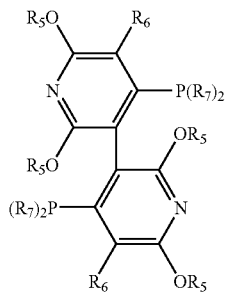

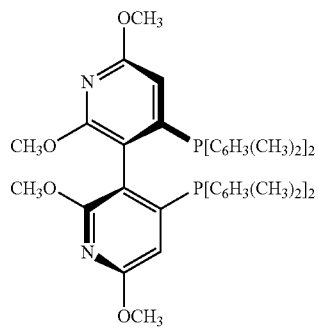

wherein R_5 is hydrogen or alkyl; R_6 is hydrogen, halogen, alkyl, alkoxy, hydroxy, chiral hydroxyalkyl, amino, mono- and di-alkylamino, vinyl or allyl; and R_7 is chosen from the following groups:

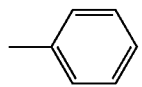 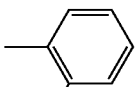 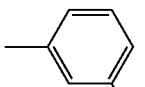

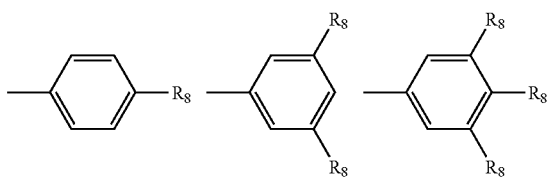

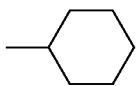

wherein $R_8$ is alkyl, alkoxy or amino, and, where there is more than one group $R_8$, each $R_8$ may be the same or different from the others; or the group $P(R_8)_2$, may form a group chosen from the following:

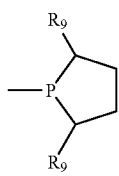 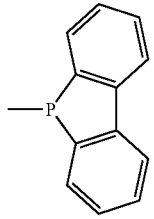

wherein $R_9$ is alkyl.

In an embodiment, the bisphosphine is (S)- or (R)-PPhos.

Preferably, the bisphosphine is (S)-(−)- or (R)-(+)-2,2',6,6'-tetramethoxy-4,4'-bis(di(3,5-xylyl)phosphino)-3,3'-bipyridine of the following formula Suitably, the bisphosphine is ((R)-(+)-2,2',6,6'-tetramethoxy-4,4'-bis(di(3,5-xylyl)phosphino)-3,3'-bipyridine).

In an embodiment, X' is chloride. In another embodiment, Y is chloride. Both X' and Y may be chloride. In another embodiment, arene is p-cymene or benzene. One particular catalyst of interest is [RuCl(R)-TolBINAP(p-cymene)]Cl, which can be formed from (R)-TolBINAP (CA RN 99646-28-3) and dichloro-(p-cymene)-ruthenium (II) dimer (CA RN 52462-29-0).

Preferably, L is acac. Suitably, L' is dmf. Other options for the ligand include acetyl, trifluoroacetyl, tetrafluoroborate, and mono- and diamines.

Most preferably, the complex has the formula [((R)-(+)-2,2',6,6'-tetramethoxy-4,4'-bis(di(3,5-xylyl)phosphino)-3,3'-bipyridine)Ru(acac)_2]. Alternatively, the complex has the formula [((R)-(+)-2,2',6,6'-tetramethoxy-4,4'-bis(di(3,5-xylyl)phosphino)-3,3'-bipyridine)RuCl_2(dmf)_2].

In an embodiment, the hydrogenation is carried out in the presence of an acid. Optionally, the acid is HBF_4, HCl, HBr, CF_3SO_3H, CH_3COOH or H_3PO_4. Preferably, the acid is H_3PO_4.

In an embodiment, the acid is present in a solvent. For example, the acid solvent is diethyl ether or water.

In an embodiment, the compound B/acid molar ratio ranges from 3.5/1 to 4/1. Suitably, the compound B/acid molar ratio ranges from 3.8/1 to 4/1. Preferably, the compound B/acid molar ratio ranges from 3.9/1 to 4/1. More preferably, the compound B/acid molar ratio is 4/1.

In another embodiment, the compound B/catalyst molar ratio ranges from 100/1 to 1000/1. Suitably, the compound B/catalyst molar ratio ranges from 250/1 to 1000/1. Preferably, the compound B/catalyst molar ratio ranges from 500/1 to 1000/1. More preferably, the compound B/catalyst molar ratio ranges from 750/1 to 1000/1. Most preferably, the compound B/catalyst molar ratio is 1000/1.

The hydrogenation may be carried out in the presence of a solvent. For example, the hydrogenation solvent is selected from a substituted or unsubstituted straight- or branched-chain $C_1$ to $C_6$ alcohol, an arene or mixtures thereof. Optionally, the solvent is selected from MeOH, EtOH, ^iPrOH, 1-PrOH, 1-BuOH, 2-BuOH, CF_3CH_2OH, DCM (dichloromethane), DCE (dichloroethane), THF (tetrahydrofuran), toluene or a 1:1 mixture of MeOH and DCM.

The hydrogenation may be carried out at a temperature ranging from 30° C. to 70° C. Suitably, the hydrogenation is carried out at a temperature ranging from 40° C. to 60° C. Preferably, the hydrogenation is carried out at a temperature ranging from 50° C. to 60° C. More preferably, the hydrogenation is carried out at a temperature of 60° C.

The hydrogenation may be carried out at a pressure ranging from 10 bars to 30 bars. Suitably, the hydrogenation is carried out at a pressure ranging from 20 bars to 30 bars. Preferably, the hydrogenation is carried out at a pressure of 30 bars.

In a further embodiment, the process further comprises subsequently recrystallising the compound of formula A. Optionally, the recrystallisation is carried out in DCM/hexane.

In an embodiment, compound A is in the form of the S enantiomer. In an alternative embodiment, compound A is in the form of the R enantiomer.

In a still further embodiment, the process further comprises converting the R or S enantiomer of compound A to the respective R or S enantiomer of a compound of formula C, or a salt thereof.

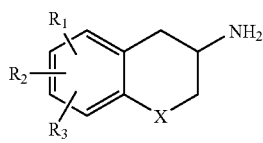

C

For example, the R or S enantiomer of compound A is converted to the respective R or S enantiomer of the compound of formula C by hydrolysis. Hydrolysis may be carried out using 40% potassium hydroxide in methanol, followed by isolation of the crude amine and crystallisation of the amine as a salt with L-tartaric acid.

Alternative methods of converting compound A to C are possible, depending on the nature of $R_4$. For example, the following processes may be used: mild acidic cleavage (in the presence of, for example, trifluoroacetic acid, HCl/EtOAc, or HBr/AcOH), acidic hydrolysis (strong aqueous acid with or without solvent), catalytic hydrogenolysis (Pd/C with a hydrogen source), etc. A comprehensive list of carbamates and methods for their cleavage can be found, for example, in Protective Groups in Organic Synthesis/Theodora W. Green and Peter G. M. Wuts, $2^{nd}$ ed., Wiley-Interscience 1991, p. 315-348.

In a yet further embodiment, the process further comprises reacting the R or S enantiomer of the compound of formula C, or a salt thereof, to produce the respective R or S enantiomer of a compound of formula E or a salt thereof.

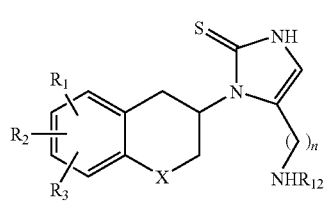

E

In broad terms, the compound C can be converted to the compound E by using the compound C as an amino component to build the N(1) moiety of the substituted imidazole-2-thione ring of compound E. More specifically, the amino group on the compound C may be converted to a 5-substituted imidazole-2-thione ring, and the group substituted at the 5 position may be converted to the group —$(CH_2)_n$—$NHR_{12}$.

In one embodiment, the R or S enantiomer of the compound of formula C, or a salt thereof, is reacted with a compound of formula D1

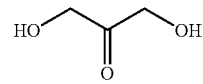

D1 to form a compound of formula D3

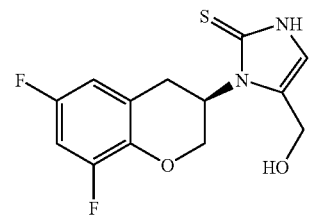

D3 followed by reaction of D3 with a dialkyl malonate and a base in the presence of a solvent, to form a compound of formula D4

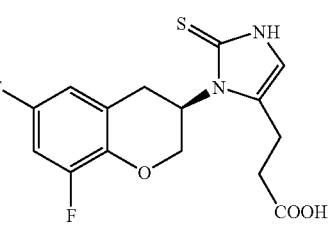

D4 followed by reaction of D4 with a suitable azide in the presence of a solvent, and then reaction with hydrochloric acid to form a compound of formula E.

In a further embodiment, the R or S enantiomer of the compound of formula C is reacted with a compound of formula D2

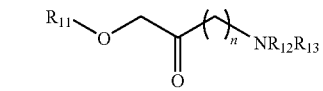

D2 to produce the respective R or S enantiomer of a compound of formula E or a salt thereof

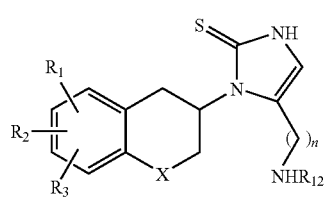

E where n signifies 1, 2 or 3; $R_{12}$ signifies hydrogen, alkyl or alkylaryl group, $R_{11}$ signifies a hydroxyl protecting group and $R_{13}$ signifies an amino protecting group, or $R_{11}$ is defined as above but $R_{12}$ and $R_{13}$ taken together represent a phthalimido group; with a water soluble thiocyanate salt in the presence of an organic acid in a substantially inert solvent, followed by subsequent deprotection of the intermediate products F to I:

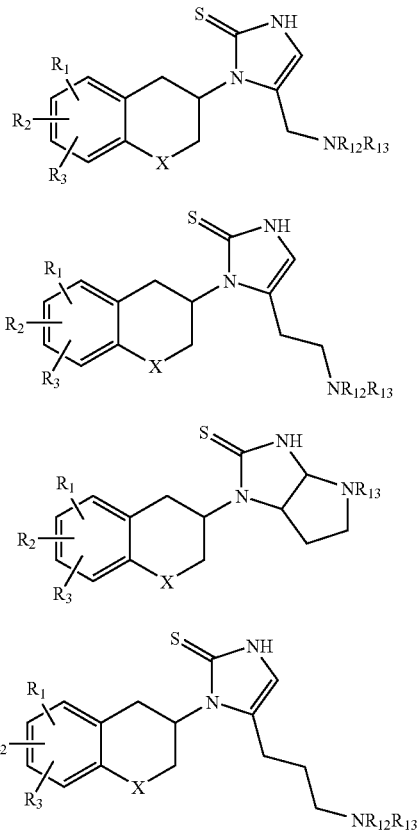

Preferably, the water soluble thiocyanate salt is an alkali metal thiocyanate salt or a tetraalkylammonium thiocyanate salt. Preferably the solvent is an organic solvent.

In an embodiment, X is O. In another embodiment, n is 2 or 3. Preferably X is O and n is 2 or 3. In a further embodiment, at least one of $R_1$, $R_2$ and $R_3$ is fluorine. Optionally, the product of the reaction of the R or S enantiomer of the compound of formula C and the compound of formula D is (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(6-hydroxychroman-3-yl)-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-(6-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-5-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (S)-5-(3-aminopropyl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione.

The product of the reaction of the R or S enantiomer of the compound of formula C and the compound of formula D may also be a salt of (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(6-hydroxychroman-3-yl)-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-(6-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-5-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (S)-5-(3-aminopropyl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione;

(R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione. Preferably the salt is the hydrochloride salt.

Alternatively, the product of the reaction of the R or S enantiomer of the compound of formula C and the compound of formula D is the respective R or S enantiomer of the compound of formula P.

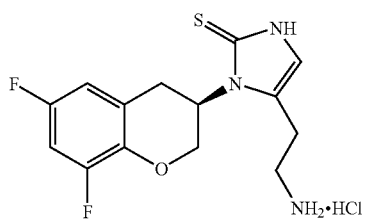

P

According to a second aspect of the present invention, there is provided a compound of formula B

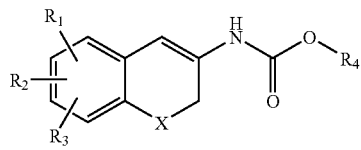

B wherein: X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

In one embodiment, X is O. In another embodiment, at least one of $R_1$, $R_2$ and $R_3$ is fluorine. Suitably, compound B has the following formula:

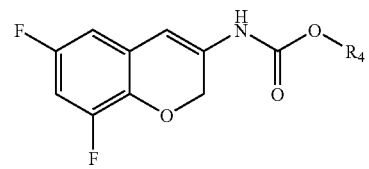

In an embodiment, $R_4$ is $C_1$ to $C_4$ alkyl. Optionally, $R_4$ is methyl (i.e. the methyl-substituted ene-carbamate), ethyl (i.e. the ethyl-substituted ene-carbamate) or t-Bu (i.e. the t-Bu-substituted ene-carbamate). Preferably, $R_4$ is methyl. In an alternative embodiment, $R_4$ is benzyl (i.e. the benzyl-substituted ene-carbamate).

According to another aspect of the present invention, there is provided the use of a chiral catalyst comprising a transition metal complex comprising a chiral ligand in the asymmetric hydrogenation of a compound of formula B,

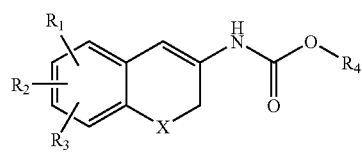

B wherein compound B is as described above.

The catalyst may have the formula [(bisphosphine)Ru(arene)X']Y, [(bisphosphine)Ru(L)$_2$] or [(bisphosphine)Ru(L')$_2$X'$_2$], as described above.

According to a further aspect of the present invention, there is provided a compound of formula A, the compound being in the form of the substantially pure R enantiomer, the substantially pure S enantiomer, or a mixture of the R and S enantiomers

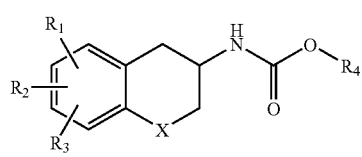

A wherein X, $R_1$, $R_2$, $R_3$ and $R_4$ have the same meanings as defined above.

As used herein, the term "substantially pure" refers to a percentage purity of at least 95%, preferably at least 98%, more preferably at least 99%, most preferably 100%. Substantially pure can be defined as ≥95% pure.

In an embodiment, X is O. In another embodiment, at least one of $R_1$, $R_2$ and $R_3$ is fluorine. Optionally, compound A has the following formula:

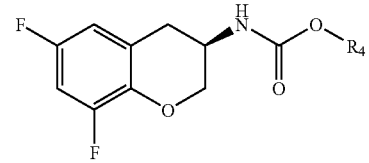

In an embodiment, $R_4$ is $C_1$ to $C_4$ alkyl. Optionally, $R_4$ is methyl, ethyl or t-Bu. Preferably, $R_4$ is methyl. In an alternative embodiment, $R_4$ is benzyl.

In an embodiment, compound A is in the form of the R enantiomer. In an alternative embodiment, compound A is in the form of the S enantiomer. In a further embodiment, compound A is in the form of a mixture of the R and S enantiomers. Optionally, the mixture is a racemic mixture.

According to a further aspect of the present invention, there is provided a transition metal complex comprising a ligand of (R)-(+)-2,2',6,6'-tetramethoxy-4,4'-bis(di(3,5-xylyl)phosphino)-3,3'-bipyridine (compound J):

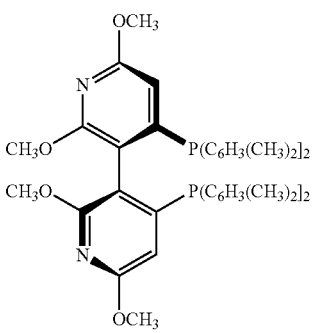

In an embodiment, the complex has the formula [((R)-(+)-2,2',6,6'-tetramethoxy-4,4'-bis(di(3,5-xylyl)phosphino)-3,3'-bipyridine)Ru(arene)X']Y, [((R)-(+)-2,2',6,6'-tetramethoxy-4,4'-bis(di(3,5-xylyl)phosphino)-3,3'-bipyridine)Ru(L)$_2$] or [((R)-(+)-2,2',6,6'-tetramethoxy-4,4'-bis(di(3,5-xylyl)phosphino)-3,3'-bipyridine)Ru(L')$_2$X'$_2$], wherein X' is a singly-negative monodentate ligand, Y is a balancing anion, L is a doubly-negative bidentate ligand and L' is a non-ionic monodentate ligand.

In an embodiment, X' is chloride. In another embodiment Y is chloride. Both X' and Y may be chloride. In another embodiment, arene is p-cymene or benzene. In a further embodiment, L is acac. Optionally, L' is dmf Other options for the ligand include acetyl, trifluoroacetyl, tetrafluoroborate, and mono- and diamines.

In a further embodiment, the complex has the formula [((R)-(+)-2,2',6,6'-tetramethoxy-4,4'-bis(di(3,5-xylyl)phosphino)-3,3'-bipyridine)RuCl$_2$(dmf)$_2$]

In an embodiment, the complex is suitable for use as a catalyst.

According to a further aspect of the present invention, there is provided (R)-(+)-2,2',6,6'-tetramethoxy-4,4'-bis(di(3,5-xylyl)phosphino)-3,3'-bipyridine (compound D):

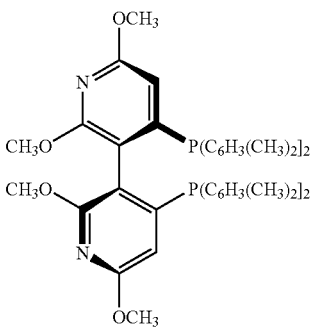

Ru-catalysed hydrogenation investigations have revealed that full conversion and e.e's up to 90% were obtained using the methyl- and ethyl-substituted ene-carbamate in the presence of Ru(Xyl-P-Phos)-based catalysts.

The reactivity and enantioselectivity in the asymmetric hydrogenation of the ene carbamate substrates has been found to vary in the order OBn<O$^t$Bu<OEt<OMe.

The methyl-substituted ene-carbamate exhibited similar conversions and e.e.'s to the ethyl-substituted ene-carbamate, although the methyl-substituted ene-carbamate was found to be slightly more reactive than the ethyl-substituted ene-carbamate. Furthermore, on recrystallisation of the hydrogenated product, a higher enantiopurity upgrade was found for products produced from methyl-substituted ene-carbamate hydrogenation than ethyl-substituted ene-carbamate hydrogenation. Thus, the methyl-substituted ene-carbamate may be preferred over the ethyl-substituted ene-carbamate because of the combination of good activity, selectivity and the ease of enantiopurity upgrade by recrystallisation.

Asymmetric hydrogenation using a rhodium-based catalyst has also been investigated. In particular, [Rh-(bisphosphine)(L)]X" cationic complexes (where L=cyclooctadiene, and X"=BF$_4$, OTf) have been investigated. Rh-bisphosphine catalysed hydrogenation revealed moderate to high activity and low enantioselectivity for the ene-carbamate substrates.

EXAMPLES

The invention will now be described with reference to the following examples.

Experimental Examples

An investigation of the effect of the catalyst on the enantioselective hydrogenation of the prochiral ene-carbamates 1a-c (as shown in Scheme 2 below) was carried out using ruthenium-bisphosphine-based catalysts (Tables 1 to 4) and rhodium-bisphosphine-based catalysts (Table 5). Initial tests were performed in MeOH at a substrate to catalyst molar ratio (S/C) of 100/1, under 30 bar H$_2$ pressure. The reactions were run in an 8-well parallel pressure hydrogenator Argonaut Endeavour.

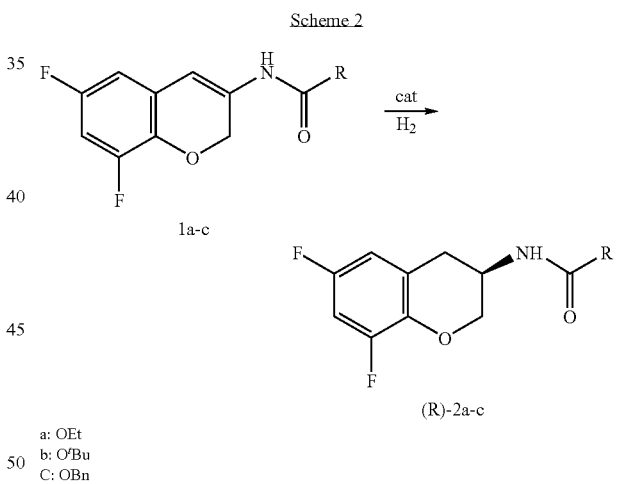

Scheme 2 a: OEt
b: O$^t$Bu
c: OBn where R=a, b, or c, accordingly.

Ruthenium-Bisphosphine Catalysis

In the case of RuCl$_2$(Ar—P-Phos)(dmf)$_2$ catalysts, the activity was substrate dependent and varied as follows: OEt≈$^t$Bu>OBn (Table 1, entry 1, Table 2, entry 1, and Table 3, entry 1. The enantioselectivity was observed to be substrate dependent, with the ethyl substituted ene-carbamate 1a resulting in the highest e.e (Table 1, entry 4, Table 2, entry 4, and Table 3, entry 3).

Generally ruthenium-Arene-P-Phos catalysts bearing chloride anionic ligands were found to be most selective (Table 1, entry 1, Table 2, entry 4, and Table 3, entry 3).

One particular catalyst, Ru(R-Xyl-P-Phos)(acac)$_2$ gave full conversion and 90% e.e when the ethyl ene carbamate 1a was employed.

HPLC conversion and enantioselectivity for substrate 1b was not determined in some cases, since the substrate 1b and the R-carbamate overlap. Attempts to optimise the HPLC methods lead to no change in the area ratio of (1b+(R)-2b) to (S)-2b. An accurate enantioselectivity determination in the case of this substrate is currently possible only when the reaction reaches full conversion (e.g. Table 2, entries 1 and 4, when the enantioselectivity values at 254 and 210 nm are consistent).

In some instances, a byproduct eluting at approximately 3 min was observed. While this byproduct has not yet been identified, it could be the result of either poor stability of these ene-carbamates in solution under prolonged reaction time or of their reaction with the alcoholic solvent.

$Ru(COD)(bismethylallyl)_2$ and $Ru(COD)(CF_3COO)_2$ (COD=η-1,5-cyclooctadiene) precursors in combination with bisphosphine ligands have been tested in the hydrogenation of substrate 1a. Generally, the activity and selectivity of the catalysts generated from these ruthenium precursors was found to be low (Table 4).

TABLE 1

Asymmetric hydrogenation of 1a using Ru-bisphosphine-based catalysts.[a]

| Entry | Catalyst | Conv (%) ($^1$HNMR)[c] | Conv (%) (HPLC, 254 nm) | Conv (%) (HPLC, 210 nm) | e.e. (%)[b] (210 nm) |
|---|---|---|---|---|---|
| 1 | $RuCl_2$—(R)—P-Phos-$(dmf)_2$ | >99 | 90 | 98 | 81(R) |
| 2 | $RuCl_2$—(S)—P-Phos-$(dmf)_2$ | 49 | 10 | 31 | 36(S) |
| 3 | $RuCl_2$—(R)-MeBoPhoz-$(dmf)_2$ | 12 | 10 | 15 | 83(R) |
| 4 | $RuCl_2$—(R)-Xyl-P-Phos-$(dmf)_2$ | 99 | >99 | >99 | 88(R) |
| 5 | $RuCl_2$—(R)-Xyl-Phane-Phos-$(dmf)_2$ | NA | 21 | 48 | 13(S) |
| 6 | $RuCl_2$—(R)-Phane-Phos-$(dmf)_2$ | NA | 8 | 26 | <5 |
| 7 | [RuCl(S)—P-Phos(p-cym)]Cl | 33 | 7 | 16 | 73(S) |
| 8 | [RuCl(S)—P-Phos(benzene)]Cl | 92 | 60 | 86 | 71(S) |
| 9 | [RuCl(R)-Xyl-P-Phos(p-cym)]Cl | 38 | 8 | 20 | 74(R) |
| 10 | [RuCl(R)-TolBINAP(p-cym)]Cl | 80 | 33 | 66 | 85(R) |
| 11 | [RuCl(S)-BINAP(p-cym)]Cl | 77 | 28 | 63 | 84(S) |
| 12 | $RuCl(R)$-Xyl-P-Phos$(acac)_2$ | >99 | >99 | >99 | 90(R) |
| 13 | $RuCl(S)$—P-Phos$(acac)_2$ | 82 | 31 | 67 | 83(S) |

[a]Reaction conditions: 0.3 mmol 1a, 0.003 mmol catalyst (S/C = 100/1), 3 mL MeOH, 60° C., 30 bar $H_2$, unoptimised reaction time 20 hrs.
[b]e.e. was determined using Diacel ChiralPak AD column, 70% MeOH: 30% IPA, 0.5 mL/min.
[c]NA = not available

TABLE 2

Asymmetric hydrogenation of 1b using Ru-bisphosphine-based catalysts.[a]

| Entry | Catalyst | Conv (%) ($^1$HNMR) | e.e. (%)[b,c] |
|---|---|---|---|
| 1 | $RuCl_2$-(R)-P-Phos-$(dmf)_2$ | >99 | 81 (R) |
| 2 | $RuI_2$-(S)-P-Phos-$(dmf)_2$ | 47 | ND |
| 3 | $RuCl_2$-(R)-MeBoPhoz-$(dmf)_2$ | 58 | ND |
| 4 | $RuCl_2$-(S)-Xyl-P-Phos-$(dmf)_2$ | >99 | 80 (S) |
| 5 | [RuCl(S)-P-Phos(p-cym)]Cl | 41 | ND |
| 6 | [RuCl(S)-P-Phos(benzene)]Cl | 92 | ND |
| 7 | [RuCl(R)-Xyl-P-Phos(p-cym)]Cl | 73 | ND |
| 8 | [RuCl(R)-TolBINAP(p-cym)]Cl | 94 | ND |
| 9 | [RuCl(S)-BINAP(p-cym)]Cl | 90 | ND |
| 10 | $RuCl(R)$-Xyl-P-Phos$(acac)_2$ | <5 | ND |

[a]Reaction conditions: 0.3 mmol substrate, 0.003 mmol catalyst (S/C = 100/1), 3 mL MeOH, 60° C., 30 bar $H_2$, unoptimised reaction time 20 hrs.
[b]e.e. was determined using Diacel ChiralPak AD column, 70% MeOH: 30% IPA, 0.5 mL/min.
[c]ND = not determined.

TABLE 3

Asymmetric hydrogenation of 1c using Ru-bisphosphine-based catalysts.[a]

| Entry | Catalyst | Conv (%) ($^1$HNMR) | Conv (%) (HPLC, 254 nm) | Conv (%) (HPLC, 210 nm) | e.e. (%)[b] (210 nm) |
|---|---|---|---|---|---|
| 1 | $RuCl_2$—(S)—P-Phos-$(dmf)_2$ | NA[c] | <10 | 38 | 46(S) |
| 2 | $RuCl_2$—(S)-MeBoPhoz-$(dmf)_2$ | <5 | 5 | 5 | 0 |
| 3 | $RuCl_2$—(R)-Xyl-P-Phos-$(dmf)_2$ | 93 | 36 | 73 | 73(R) |

[a]Reaction conditions: 0.3 mmol substrate, 0.003 mmol catalyst (S/C = 100/1), 3 mL MeOH, 60° C., 30 bar $H_2$, unoptimised reaction time 20 hrs.
[b]e.e. was determined using Diacel ChiralPak AD column, 70% MeOH: 30% IPA, 0.5 mL/min.
[c]NA = not available.

TABLE 4

Asymmetric hydrogenation of 1a using in situ Ru-bisphosphine-based catalysts.[a]

| Entry | Ru precursor/ ligand | Conv (%) (HPLC, 254 nm) | Conv (%) (HPLC, 210 nm) | e.e. (%)[b] (210 nm) |
|---|---|---|---|---|
| 1 | $Ru(COD)(bismethylallyl)_2$/(R)-Xyl-P-Phos | 12 | 41 | 34 (R) |
| 2 | $Ru(COD)(bismethylallyl)_2$/(R)-MeBoPhoz | <5 | <5 | — |
| 3 | $Ru(COD)(bismethylallyl)_2$/(R)-Xyl-Phane-Phos | 24 | 59 | 9 (S) |
| 4 | $Ru(COD)(CF_3COO)_2$/(R)-MeBoPhoz | 6 | 20 | <5 |
| 5 | $Ru(COD)(CF_3COO)_2$/(R)-Xyl-Phane-Phos | 10 | 37 | <5 |

[a]Reaction conditions: 0.3 mmol 1a, 0.003 mmol catalyst ruthenium precursor, 0.0036 mmol ligand stirred in 1 mL MeOH at 60° C. for 0.5 hrs(S/C = 100/1), 3 mL MeOH, 60° C., 30 bar $H_2$, unoptimized reaction time 20 hrs.
[b]e.e. was determined using Diacel ChiralPak AD column, 70% MeOH: 30% IPA, 0.5 mL/min.

Rhodium-Bisphosphine Catalysis

Hydrogenation of ene-carbamates 1a-c using catalysts of general formula [Rh(bisphosphine)(COD)]X (X=$BF_4$, OTf), where bisphosphine is Xyl-P-Phos, P-Phos, Xyl-PhanePhos, PhanePhos, MeBophoz, Spiro-P, H8-BINAM-P in methanol at S/C 100, 60° C., 30 bar $H_2$ led to low enantioselectivities (Table 5).

TABLE 5

Asymmetric hydrogenation using Rh-bisphosphine-based catalysts.[a]

| Entry | Ru precursor/ ligand | substrate | Conv (%) (HPLC, 254 nm) | Conv (%) (HPLC, 210 nm) | e.e. (%)[b] (210 nm) |
|---|---|---|---|---|---|
| 1 | [Rh(COD)(R-BINAM-P)]BF$_4$ | 1a | 9 | 35 | <5 |
| 2 | [Rh(COD)(R-BINAM-P)]BF$_4$ | 1b | ND | ND | ND |
| 3 | [Rh(COD)(R-BINAM-P)]BF$_4$ | 1c | 37 | 77 | <5 |
| 4 | [Rh(COD)(R-Spiro-P)]BF$_4$ | 1a | 95 | 98 | <5 |
| 5 | [Rh(COD)(R-Spiro-P)]BF$_4$ | 1b | >99 | >99 | <5 |
| 6 | [Rh(COD)(R-Spiro-P)]BF$_4$ | 1c | >99 | >99 | <5 |
| 7 | [Rh(COD)(R-Phane-Phos)]BF$_4$ | 1a | >99 | >99 | <5 |
| 8 | [Rh(COD)(R-Phane-Phos)]BF$_4$ | 1c | >99 | >99 | <5 |
| 9 | [Rh(COD)$_2$]OTf/(R)-MeBoPhoz | 1a | 17 | 49 | 40(S) |
| 10 | [Rh(COD)$_2$]OTf/ 4-F-Ph-(R)-MeBoPhoz | 1a | <5 | <5 | <5 |
| 11 | [Rh(COD)$_2$]OTf/(R)-BnBoPhoz | 1a | 10 | 33 | 25(S) |
| 12 | [Rh(COD)$_2$]OTf/(R)-Spiro-P | 1a | <5 | <5 | <5 |
| 13 | [Rh(COD)$_2$]OTf/(R)—H8-BINAM-P | 1a | 30 | 64 | <5 |
| 14 | [Rh(COD)$_2$]OTf/(S)-PhanePhos | 1a | >99 | >99 | <5 |
| 15 | [Rh(COD)$_2$]OTf/(R)-Xyl-PhanePhos | 1a | >99 | >99 | <5 |

[a]Reaction conditions: 0.3 mmol substrate, 0.003 mmol catalyst (or 0.003 rhodium precursor, 0.0036 mmol ligand stirred in 1 mL MeOH at r.t. for 0.5 hrs(S/C = 100/1), 3 mL MeOH, 60° C., 30 bar H$_2$, unoptimised reaction time 20 hrs.
[b]e.e. was determined using Diacel ChiralPak AD column, 70% MeOH: 30% IPA, 0.5 mL/min.

Solvent, Temperature, and Pressure Optimisation

The reaction shown in Scheme 3 was studied in order to determine the influence of solvent, temperature, and pressure in the Ru(R)-Xyl-P-Phos(acac)-2-catalysed asymmetric hydrogenation of 1a.

The study showed that, at S/C 100 (Table 6), MeOH is the solvent of choice, giving the highest enantioselectivity (Table 6, entries 1-11). Moreover, temperature and pressure experiments in MeOH showed that the activity was both temperature dependent (Table 6, entries 1, 12 and 15) and pressure dependent at low temperatures (Table 6, entries 15 and 16 (low T) vs. entries 1 and 17 (higher T)). Notably, the enantioselectivity of the reaction is neither temperature nor pressure dependent (Table 6, entries 1, 15 and 17).

Scheme 3

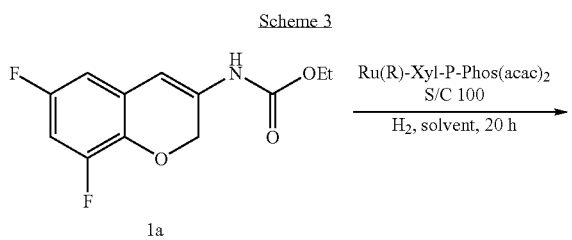

1a

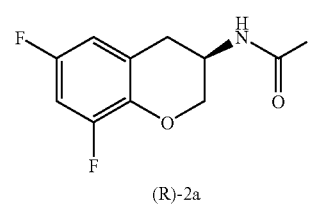

(R)-2a

TABLE 6

Influence of Solvent, Temperature, and Pressure in the Ru(R)-Xyl-P-Phos(acac)$_2$-catalysed Asymmetric Hydrogenation of 1a.[a]

| Entry | Solvent | T (° C.) | P (bar) | Conv (%) (254 nm) | Conv (%) (210 nm) | e.e. (%)[b] (210 nm) |
|---|---|---|---|---|---|---|
| 1 | MeOH | 60 | 30 | >99 | >99 | 90(R) |
| 2 | EtOH | 60 | 30 | 88 | 97 | 82(R) |
| 3 | $^i$PrOH | 60 | 30 | 21 | 70 | 78(R) |
| 4 | 1-PrOH | 60 | 30 | 50 | 90 | 76(R) |
| 5 | 1-BuOH | 60 | 30 | 32 | 70 | 71(R) |
| 6 | 2-BuOH | 60 | 30 | 20 | 47 | 66(R) |
| 7 | CF$_3$CH$_2$OH | 60 | 30 | >99 | >99 | 56(R) |
| 8 | DCM | 60 | 30 | >99 | >99 | 71(R) |
| 9 | DCE | 60 | 30 | 65 | 88 | 64(R) |
| 10 | THF | 60 | 30 | <5 | <10 | — |
| 11 | Tol | 60 | 30 | >99 | >99 | 76(R) |
| 12 | MeOH | 30 | 30 | <5 | <10 | — |
| 13 | DCM | 30 | 30 | 17 | 54 | 72(R) |
| 14 | MeOH/DCM 1/1 | 30 | 30 | 11 | 40 | 88(R) |
| 15 | MeOH | 40 | 30 | 71 | 92 | 90(R) |
| 16 | MeOH | 40 | 10 | <5 | 13 | — |
| 17 | MeOH | 60 | 10 | >99 | >99 | 90(R) |

[a]Reaction conditions: 0.3 mmol 1a, 0.003 mmol catalyst (S/C = 100/1), 3 mL solvent, unoptimised reaction time 20 hrs.
[b]e.e. was determined using Diacel ChiralPak AD-H column, 70% MeOH: 30% IPA, 0.5 mL/min.

Concentration Optimisation

Concentration optimisation experiments in the Ru-catalysed asymmetric hydrogenation (see Scheme 4 below) were performed at substrate to catalyst ratio of 500/1. As shown in Table 7, moderate conversion was obtained at S/C 500 and 0.5M substrate concentration and in the presence of Ru(R-Xyl-P-Phos)(acac)$_2$ (entry 1).

Scheme 4

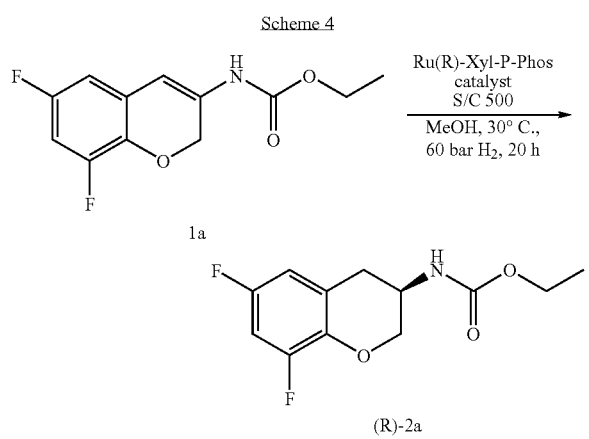

TABLE 7

Concentration Optimisation in the Ru-catalysed Asymmetric Hydrogenation of 1a.[a]

| Entry | Catalyst | [S] (mmol/ mL) | Conv (%) (254 nm) | Conv (%) (210 nm) | e.e. (%)[b] (210 nm) |
|---|---|---|---|---|---|
| 1 | Ru(R)-Xyl-P-Phos(acac)$_2$ | 0.5 | 21 | 60 | 92(R) |
| 2 | RuCl$_2$—(R)-Xyl-P-Phos-(dmf)$_2$ | 0.5 | 13 | 42 | 92(R) |
| 3 | Ru(R)-Xyl-P-Phos(acac)$_2$ | 1 | 9 | 36 | 91(R) |
| 4 | RuCl$_2$—(R)-Xyl-P-Phos-(dmf)$_2$ | 1 | 10 | 17 | 88(R) |

[a]Reaction conditions: 0.3 mmol 1a, S/C = 500/1, MeOH, unoptimised reaction time 20 hrs.
[b]e.e. was determined using Diacel ChiralPak AD-H column, 70% MeOH: 30% IPA, 0.5 mL/min.

Substrate Purity

Substrate 1a of higher purity than that used in the [(bisphosphine)RuLX$_2$] catalysis experiment (see Table 1) was tested in the asymmetric hydrogenation using a series of Ru-bisphosphine based catalysts (Table 8).

Generally, in the case of ruthenium-dmf adducts a similar behaviour to the previous batch was observed (Table 8, entries 1 and 3 vs. Table 1, entries 1 and 4). A slightly higher e.e was observed in the case of Ru(R-Xyl-P-Phos)(acac)$_2$ (Table 8, entries 8 and 9 vs. Table 1, entry 12). The activity of Ru-arene based catalysts was higher when purer material was used (Table 8, entry 5 vs. Table 3a, entry 7, Table 8, entry 6 vs. Table 1, entry 9). [RuCl(R-Tol-BINAP)(p-cymene)]Cl showed not only an increased activity, but also improved enantioselectivity (Table 8, entry 7 vs. Table 1, entry 10), while Ru(S—P-Phos)(acac)$_2$ catalyst led to no conversion to the hydrogenated product (Table 8, entry 10 vs. Table 1, entry 13).

TABLE 8

Asymmetric hydrogenation of 1a using Ru-bisphosphine-based catalysts.[a]

| Entry | Catalyst | Conv (%) (254 nm) | Conv (%) (210 nm) | e.e. (%)[b] |
|---|---|---|---|---|
| 1 | RuCl$_2$-(R)-P-Phos-(dmf)$_2$ | 91 | 98 | 79 (R) |
| 2 | RuCl$_2$-(R)-MeBoPhoz-(dmf)$_2$ | <5 | <5 | — |
| 3 | RuCl$_2$-(R)-Xyl-P-Phos-(dmf)$_2$ | >99 | >99 | 84 (R) |
| 4 | [RuCl(S)-P-Phos(benzene]Cl | 61 | 89 | 79 (S) |
| 5 | [RuCl(R)-P-Phos(p-cym)]Cl | 40 | 80 | 79 (R) |
| 6 | [RuCl(R)-Xyl-P-Phos(p-cym)]Cl | 98 | 99 | 89 (R) |
| 7 | [RuCl(R)-TolBINAP(p-cym)]Cl | 96 | 99 | 92 (R) |
| 8 | Ru(R)-Xyl-P-Phos(acac)$_2$ | 93 | 99 | 92 (R) |
| 9 | Ru(R)-Xyl-P-Phos(acac)$_2$ | 97 | 99 | 92 (R) |
| 10 | Ru(S)-P-Phos(acac)$_2$ | <5 | <5 | — |

[a]Reaction conditions: 0.3 mmol 1a, 0.003 mmol catalyst (S/C = 100/1), 3 mL MeOH, 60° C., 30 bar H$_2$, unoptimised reaction time 20 hrs.
[b]e.e. was determined using Diacel ChiralPak AD-H column, 70% MeOH: 30% IPA, 0.5 mL/min.

Methyl-Substituted Ene-Carbamate

The methyl-substituted ene-carbamate 1d was investigated in a similar Ru-bisphosphine catalyst screening. The racemate 2d was obtained via Pd/C-catalysed hydrogenation of 1d (Scheme 5 below).

Scheme 5

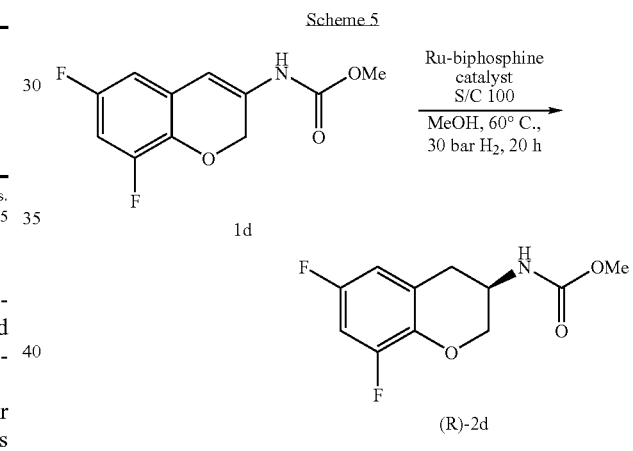

The results in Table 9 show that substrate 1d presents similar activity and enantioselectivity to substrate 1a. Ru(R-Xyl-P-Phos)(acac)$_2$ showed no activity (Table 9, entry 9). Without wishing to be bound by theory, the catalyst behaviour could be strongly dependent on the type and level of impurities present in the material.

TABLE 9

Asymmetric hydrogenation of 1d using Ru-bisphosphine-based catalysts.[a]

| Entry | Catalyst | Conv (%) (254 nm) | Conv (%) (210 nm) | e.e. (%)[b] |
|---|---|---|---|---|
| 1 | 10% Pd/C | 98 | >99 | rac |
| 2 | RuCl$_2$-(R)-P-Phos-(dmf)$_2$ | 87 | 97 | 80 (R) |
| 3 | RuCl$_2$-(R)-MeBoPhoz-(dmf)$_2$ | <5 | <5 | — |
| 4 | RuCl$_2$-(R)-Xyl-P-Phos-(dmf)$_2$ | >99 | >99 | 85 (R) |
| 5 | [RuCl(S)-P-Phos(benzene]Cl | 83 | 97 | 79 (S) |
| 6 | [RuCl(R)-P-Phos(p-cym)]Cl | 19 | 54 | 83 (R) |

TABLE 9-continued

Asymmetric hydrogenation of 1d using Ru-bisphosphine-based catalysts.[a]

| Entry | Catalyst | Conv (%) (254 nm) | Conv (%) (210 nm) | e.e. (%)[b] |
|---|---|---|---|---|
| 7 | [RuCl(R)-Xyl-P-Phos(p-cym)]Cl | 99 | 99 | 84 (R) |
| 8 | [RuCl(R)-TolBINAP(p-cym)]Cl | 95 | 99 | 92 (R) |
| 9 | Ru(R)-Xyl-P-Phos(acac)$_2$ | <5 | <5 | — |
| 10 | Ru(S)-P-Phos(acac)$_2$ | <5 | <5 | — |

[a]Reaction conditions: 0.3 mmol 1d, 0.003 mmol catalyst (S/C = 100/1), 3 mL MeOH, 60° C., 30 bar H$_2$, unoptimized reaction time 20 hrs.
[b]e.e. and conversions were determined using Diacel ChiralPak AD-H column, 70% MeOH: 30% IPA, 0.5 mL/min. Retention times: 1d, 10.6 min (99.3% chemical purity at 254 nm, 96.3% chemical purity at 210 nm); (R)-2d, 8.5 min; (S)-2d, 9.8 min.

Influence of Acid Additives on the Ru(R-Xyl-P-Phos)(acac)$_2$-Catalysed Hydrogenation of 1a and 1d The influence of acids on the Ru(R-Xyl-P-Phos)(acac)-2-catalysed hydrogenation was investigated. It was observed (Table 10) that the fully hydrogenated product 2d was obtained in the presence of Ru(R-Xyl-P-Phos)(acac)$_2$ catalyst and different acids. Since the test reactions were run at high catalyst loadings, there was no differentiation from activity standpoint, while the enantioselectivity was not highly dependent on the type of acid used.

TABLE 10

Asymmetric hydrogenation of 1a and 1d using Ru(R-Xyl-P-Phos)(acac)$_2$ and acid additives.[a]

| Entry | Acid | Substrate | T (° C.) | Conv (%) (254 nm) | Conv (%) (210 nm) | e.e. (%)[b] |
|---|---|---|---|---|---|---|
| 1 | — | 1a | 60 | 97 | 99 | 92(R) |
| 2 | HBF$_4$-Et$_2$O | 1a | 60 | >99 | >99 | 93(R) |
| 3 | HCl, 1M in Et$_2$O | 1a | 60 | >99 | >99 | 92(R) |
| 4 | HCl/H$_2$O | 1a | 60 | 85 | 96[c] | 86(R) |
| 5 | HBr/H$_2$O | 1a | 60 | 80 | 94[d] | 87(R) |
| 6 | CF$_3$SO$_3$H | 1a | 60 | >99 | >99 | 93(R) |
| 7 | CH$_3$COOH | 1a | 60 | >99 | >99 | 92(R) |
| 8 | H$_3$PO$_4$ | 1a | 60 | >99 | >99 | 93(R) |
| 9 | — | 1d | 60 | <5 | <5 | — |
| 10 | H$_3$PO$_4$ | 1d | 60 | >99 | >99 | 93(R) |
| 11 | H$_3$PO$_4$ | 1d | 50 | >99 | >99 | 92(R) |
| 12 | HBF$_4$-Et$_2$O | 1d | 50 | >99 | >99 | 92(R) |
| 13 | HCl, 1M in Et$_2$O | 1d | 50 | 93 | 98 | 87(R) |
| 14 | CF$_3$SO$_3$H | 1d | 50 | >99 | >99 | 92(R) |
| 15 | CH$_3$COOH | 1d | 50 | 90 | 98 | 91(R) |

[a]Reaction conditions: 0.3 mmol substrate, 0.003 mmol catalyst, 0.03 mmol acid (S/acid/C = 100/25/1), 3 mL MeOH, 30 bar H$_2$, unoptimised reaction time 20 hrs.
[b]e.e. was determined using Diacel ChiralPak AD-H column, 70% MeOH: 30% IPA, 0.5 mL/min.
[c]48% byproduct.
[d]52% byproduct Influence of Temperature The fact that the hydrogenation of 1a could be performed at lower temperatures (Table 11) in the presence of Ru(R-Xyl-P-Phos)(acac)$_2$ catalyst and H$_3$PO$_4$ as additive and the temperature independence of enantioselectivity indicated that lower catalyst loadings could be achievable. H$_3$PO$_4$ was chosen to perform catalyst loading optimisation, with the substrate to acid ratio fixed at 4 to 1.

The asymmetric hydrogenation of both substrates was performed in high conversions at substrate to catalyst ratios of 1000/1 (Table 12). As seen in Table 12, substrate 1d is slightly more reactive than 1a. Without wishing to be bound by theory, it is thought that the slightly lower enantioselectivities observed in these experiments might be due to the increased acid to catalyst ratio.

TABLE 11

Influence of Temperature on the Asymmetric Hydrogenation of 1a.[a]

| Entry | T (° C.) | Conv (%) (254 nm) | Conv (%) (210 nm) | e.e. (%)[b] |
|---|---|---|---|---|
| 1 | 60 | >99 | >99 | 93 (R) |
| 3 | 50 | >99 | >99 | 93 (R) |
| 4 | 40 | >99 | >99 | 93 (R) |
| 5 | 30 | >99 | >99 | 93 (R) |

[a]Reaction conditions: 0.3 mmol substrate 1a, 0.003 mmol catalyst, 0.03 mmol acid (S/acid/C = 100/25/1), 3 mL MeOH, 30 bar H$_2$, unoptimised reaction time 20 hrs.
[b]e.e. was determined using Diacel ChiralPak AD-H column, 70% MeOH: 30% IPA, 0.5 mL/min.

TABLE 12

Reaction Conditions Optimisation in the Asymmetric Hydrogenation of 1a and 1d using Ru(R-Xyl-P-Phos)(acac)$_2$.[a]

| Entry | Substrate | S/C | H$_3$PO$_4$/C | T (° C.) | [S] mmol/mL | Conv (%) (254 nm) | Conv (%) (210 nm) | e.e. (%)[b] |
|---|---|---|---|---|---|---|---|---|
| 1 | 1a | 100 | 25/1 | 60 | 0.1 | >99 | >99 | 93(R) |
| 2 | 1a | 750 | 190/1 | 60 | 0.33 | 82 | 95 | 89(R) |
| 3 | 1a | 1000 | 250/1 | 60 | 0.5 | >99 | >99 | 90(R) |
| 4 | 1a | 1000 | 250/1 | 70 | 0.5 | 91 | 98 | 89(R) |
| 5 | 1d | 100 | 25/1 | 60 | 0.1 | >99 | >99 | 93(R) |
| 6 | 1d | 250 | 63/1 | 60 | 0.1 | >99 | >99 | 92(R) |
| 7 | 1d | 500 | 125/1 | 60 | 0.2 | >99 | >99 | 89(R) |
| 8 | 1d | 750 | 190/1 | 60 | 0.33 | >99 | >99 | 90(R) |
| 9 | 1d | 1000 | 250/1 | 60 | 0.5 | >99 | >99 | 90(R) |
| 10 | 1d | 1000 | 250/1 | 70 | 0.5 | >99 | >99 | 90(R) |

[a]Reaction conditions: substrate, catalyst, (S/acid = 4/1), 3 mL MeOH, 30 bar H$_2$, unoptimised reaction time 20 hrs.
[b]e.e. was determined using Diacel ChiralPak AD-H column, 70% MeOH: 30% IPA, 0.5 mL/min.

Enantiopurity Upgrade

The enantiopurity of the products may be further improved by recrystallisation.

For example, reaction mixtures that reached >98% conversion and >90% e.e. were combined, and tested for enantiopurity upgrade via recrystallisation. From one recrystallisation experiment, it was found that from DCM/Hexane, the enantiopurity of product (R)-2d could be upgraded from 91% e.e to 98.7% e.e. The yield of this recrystallisation experiment was 70%. Evaporation of a MeOH solution of product 2a (approx. 91% e.e) led to a crystalline residue which was washed with DCM/Hexane=1/25 mixture. The resulting product was recovered in 75% yield and 93% e.e, indicating the enantiopurity upgrade of product 2a.

The preferred reaction conditions can be described as follows: substrate 1d (methyl substituted ene-carbamate) was reduced to the desired product in >99% conversion and 90% e.e. in the presence of Ru(R-Xyl-P-Phos)(acac)$_2$ and H$_3$PO$_4$ at substrate/acid/catalyst ratio of 1000/250/1, 0.5M substrate concentration in methanol, 60° C. and 30 bar H$_2$ pressure. Importantly, the enantiopurity of the product resulting from the catalytic step could be upgraded to 98.7% e.e. by an unoptimised recrystallisation from DCM/hexane.

Experimental Procedure for the Synthesis of [(R)-Xyl-P-Phos RuCl$_2$ (dmf)$_2$].

[Ru(benzene)Cl$_2$]$_2$ (0.147 mmol, 75 mg) and (R)-Xyl-P-Phos (0.32 mmol, 242 mg) were loaded in a 25 mL Schlenk tube and tube evacuated by performing there vacuum/N$_2$ cycles. 2 mL DMF was injected and the resulting mixture was stirred under N$_2$ at 105° C. for 2 h. The solvent was removed under high vacuum and the resulting brown solid was used in catalysis without further purification.

It will be appreciated that the invention may be modified within the scope of the appended claims.

What is claimed is:

1. A process for preparing the S or R enantiomer of a compound of formula A,

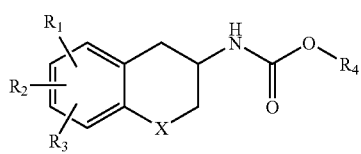

A the process comprising subjecting a compound of formula B to asymmetric hydrogenation in the presence of a chiral catalyst and a source of hydrogen wherein the chiral catalyst comprises a Ru-biphosphine metal complex,

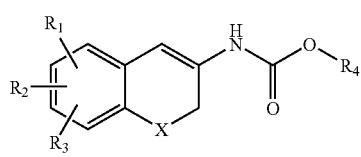

B wherein: X is oxygen; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine and wherein at least one of $R_1$, $R_2$ and $R_3$ is fluorine.

2. The process according to claim 1, wherein compound A has the following formula:

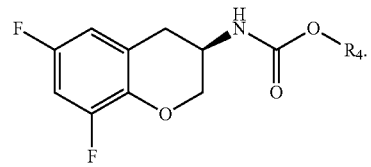

3. The process according to claim 1, wherein $R_4$ is $C_1$ to $C_4$ alkyl.

4. The process according to claim 3, wherein $R_4$ is methyl, ethyl or $^tBu$.

5. The process according to claim 4, wherein $R_4$ is methyl.

6. The process according to claim 1, wherein $R_4$ is benzyl.

7. The process according to claim 1, wherein the catalyst has the formula [(bisphosphine)Ru(arene)X']Y, [(bisphosphine)Ru(L)$_2$] or [(bisphosphine)Ru(L')$_2$X'$_2$], wherein the bisphosphine is chiral, X' is a singly-negative monodentate ligand, Y is a balancing anion, L is a doubly-negative bidentate ligand and L' is a non-ionic monodentate ligand.

8. The process according to claim 7, wherein the bisphosphine is the R or S enantiomer of BINAP or TolBINAP.

9. The process according to claim 7, wherein the bisphosphine is the R or S enantiomer of a compound having the following formula

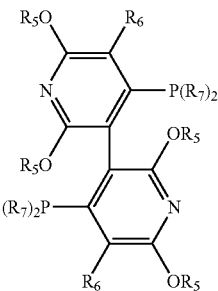

wherein $R_5$ is hydrogen or alkyl; $R_6$ is hydrogen, halogen, alkyl, alkoxy, hydroxy, chiral hydroxyalkyl, amino, mono- and di-alkylamino, vinyl or allyl; and $R_7$ is chosen from the following groups:

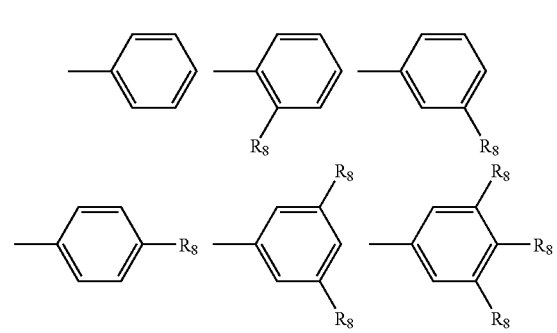

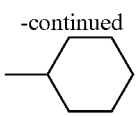

wherein R₈ is alkyl, alkoxy or amino, and, where there is more than one group R₈, each R₈ may be the same or different from the others; or the group P(R₇)₂, may form a group chosen from the following:

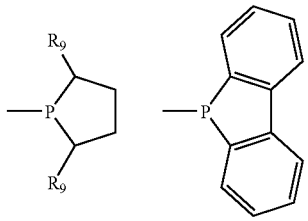

wherein R₉ is alkyl.

10. The process according to claim 9, wherein the bisphosphine is (S)- or (R)-PPhos.

11. The process according to claim 9, wherein the bisphosphine is (S)-(−)- or (R)-(+)-2,2',6,6'-tetramethoxy-4,4'-bis(di(3,5-xylyl)phosphino)-3,3'-bipyridine of the following formula:

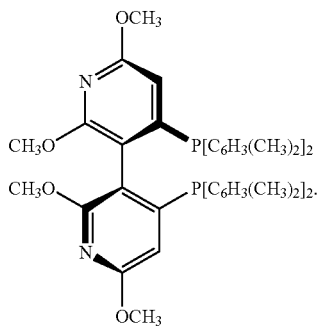

12. The process according to claim 11, wherein the bisphosphine is ((R)-(+)-2,2',6,6'-tetramethoxy-4,4'-bis(di(3,5-xylyl)phosphino)-3,3'-bipyridine).

13. The process according to claim 7, wherein X' and Y are chloride.

14. The process according to claim 7, wherein arene is p-cymene or benzene.

15. The process according to claim 7, wherein L is acac.

16. The process according to claim 7, wherein L' is dmf.

17. The process according to claim 7, wherein the complex has the formula [((R)-(+)-2,2',6,6'-tetramethoxy-4,4'-bis(di(3,5-xylyl)phosphino)-3,3'-bipyridine)Ru(acac)₂].

18. The process according to claim 7, wherein the complex has the formula [((R)-(+)-2,2',6,6'-tetramethoxy-4,4'-bis(di(3,5-xylyl)phosphino)-3,3'-bipyridine)RuCl₂(dmf)₂].

19. The process according to claim 1, wherein the hydrogenation is carried out in the presence of an acid.

20. The process according to claim 19, wherein the acid is HBF₄, HCl, HBr, CF₃SO₃H, CH₃COOH or H₃PO₄.

21. The process according to claim 20, wherein the acid is H₃PO₄.

22. The process according to claim 19, wherein the acid is present in a solvent.

23. The process according to claim 22, wherein the solvent is diethyl ether or water.

24. The process according to claim 19, wherein the compound B/acid molar ratio ranges from 3.5/1 to 4/1.

25. The process according to claim 24, wherein the wherein the compound B/acid molar ratio ranges from 3.8/1 to 4/1.

26. The process according to claim 25, wherein the wherein the compound B/acid molar ratio ranges from 3.9/1 to 4/1.

27. The process according to claim 26, wherein the wherein the compound B/acid molar ratio is 4/1.

28. The process according to claim 1, wherein the compound B/catalyst molar ratio ranges from 100/1 to 1000/1.

29. The process according to claim 28, wherein the compound B/catalyst molar ratio ranges from 250/1 to 1000/1.

30. The process according to claim 29, wherein the compound B/catalyst molar ratio ranges from 500/1 to 1000/1.

31. The process according to claim 30, wherein the compound B/catalyst molar ratio ranges from 750/1 to 1000/1.

32. The process according to claim 31, wherein the compound B/catalyst molar ratio is 1000/1.

33. The process according to claim 1, wherein the hydrogenation is carried out in the presence of a solvent.

34. The process according to claim 33, wherein the solvent is selected from a substituted or unsubstituted straight- or branched-chain C₁ to C₆ alcohol, an arene or mixtures thereof.

35. The process according to claim 34, wherein the solvent is selected from MeOH, EtOH, ⁱPrOH, 1-PrOH, 1-BuOH, 2-BuOH, CF₃CH₂OH, DCM, DCE, THF, toluene or a 1:1 mixture of MeOH and DCM.

36. The process according to claim 1, wherein the hydrogenation is carried out at a temperature ranging from 30° C. to 70° C.

37. The process according to claim 36, wherein the hydrogenation is carried out at a temperature ranging from 40° C. to 60° C.

38. The process according to claim 37, wherein the hydrogenation is carried out at a temperature ranging from 50° C. to 60° C.

39. The process according to claim 38, wherein the hydrogenation is carried out at a temperature of 60° C.

40. The process according to claim 1, wherein the hydrogenation is carried out at a pressure ranging from 10 bars to 30 bars.

41. The process according to claim 40, wherein the hydrogenation is carried out at a pressure ranging from 20 bars to 30 bars.

42. The process according to claim 1, wherein the hydrogenation is carried out at a pressure of 30 bars.

43. The process according to claim 1, further comprising subsequently recrystallising the compound of formula A.

44. The process according to claim 43, wherein the recrystallisation is carried out in DCM/hexane.

45. The process according to claim 1, wherein compound A is in the form of the S enantiomer.

46. The process according to claim 1, wherein compound A is in the form of the R enantiomer.

47. A process for preparing the R or S enantiomer of a compound of formula C,

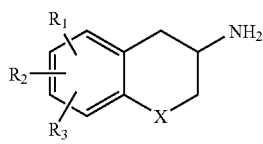

C

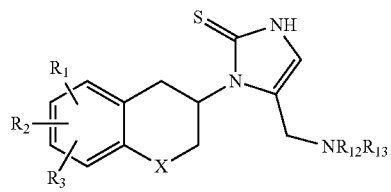

F

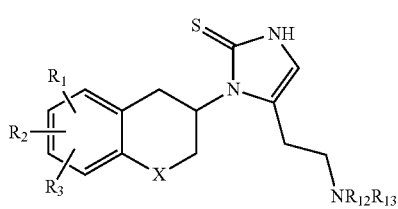

G

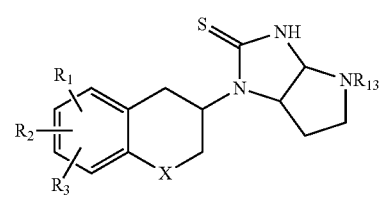

H

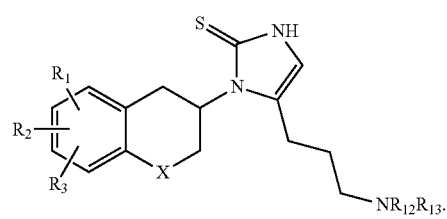

I comprising forming the R or S enantiomer of a compound of formula A by a process according to claim 1, followed by converting the R or S enantiomer of the compound A to the respective R or S enantiomer of a compound of formula C, wherein: X is oxygen; $R_1$, $R_2$ and $R_3$ are the same or different and signify hydrogens, halogens, alkyl, alkyloxy, hydroxy, nitro, alkylcarbonylamino, alkylamino or dialkylamino group; and wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine, and wherein at least one of $R_1$, $R_2$ and $R_3$ is fluorine.

48. A process for forming a R or S compound of formula E or a salt thereof:

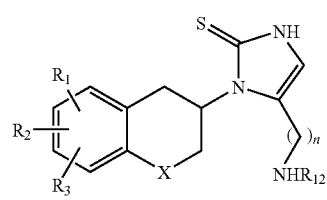

E comprising forming the R or S enantiomer of a compound of formula C according to the process of claim 47, and converting the R or S enantiomer of the compound of formula C to the R or S enantiomer of the compound of formula of formula E, wherein: n is 1, 2 or 3 and $R_{12}$ is hydrogen, alkyl or alkylaryl group.

49. The process according to claim 48, comprising reacting the R or S enantiomer of the compound of formula C with a compound of formula D2

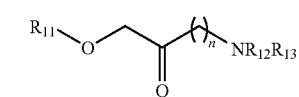

D2 where n signifies 1, 2 or 3; when n is 1 or 2, $R_{12}$ signifies hydrogen, alkyl or alkylaryl group; $R_{11}$ signifies a hydroxyl protecting group and $R_{13}$ signifies an amino protecting group; when n signifies 3, $R_{11}$ signifies a hydroxyl protecting group but $R_{12}$ and $R_{13}$ taken together represent a phthalimido group; and with a water soluble thiocyanate salt in the presence of an organic acid in a substantially inert solvent, followed by subsequent deprotection of the intermediate products F to I:

50. The process according to claim 48, wherein the compound E is (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (R)-1-(6,8-difluorochroman-3-yl)-5-(2-methylaminoethyl)-1,3-dihydroimidazole-2-thione, or a salt thereof.

51. The process according to claim 48, wherein the compound E is the respective R or S enantiomer of the compound of formula P:

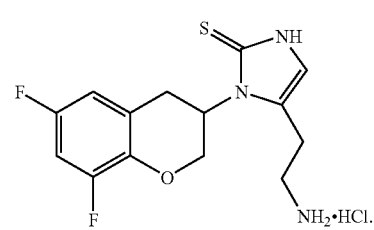

P

52. A method comprising using a chiral catalyst comprising a transition metal complex which comprises a chiral ligand in the asymmetric hydrogenation of a compound of formula B,
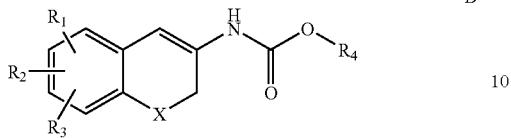
wherein X, $R_1$, $R_2$, $R_3$ and $R_4$ have the same meanings as defined in claim 1 and wherein the chiral catalyst comprises a Ru-biphosphine metal complex.
* * * * *

UNITED STATES PATENT AND TRADEMARK OFFICE
CERTIFICATE OF CORRECTION

PATENT NO.       : 8,546,571 B2
APPLICATION NO.  : 12/518416
DATED            : October 1, 2013
INVENTOR(S)      : Learmonth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 36 days.

Signed and Sealed this

Fifteenth Day of September, 2015

Michelle K. Lee
*Director of the United States Patent and Trademark Office*